United States Patent [19]
Bredesen et al.

[11] Patent Number: 5,834,457
[45] Date of Patent: Nov. 10, 1998

[54] METHOD OF MODULATING RADICAL FORMATION BY MUTANT CUZNSOD ENZYMES

[75] Inventors: Dale E. Bredesen, Rancho Santa Fe; Joan S. Valentine, Los Angeles; Martina Wiedau-Pazos, Los Angeles; Joy J. Goto, Los Angeles; Edith B. Gralla, Los Angeles, all of Calif.

[73] Assignees: The Regents of the University of California, Oakland; The Burnham Institute, La Jolla, both of Calif.

[21] Appl. No.: 592,704

[22] Filed: Jan. 26, 1996

[51] Int. Cl.$^6$ .................................................. A01N 43/04
[52] U.S. Cl. ........................... 514/188; 514/184; 514/499
[58] Field of Search ............................. 514/44, 365, 562, 514/227.2, 188, 184, 499

[56] References Cited

PUBLICATIONS

Zhong et al., "bcl–2 inhibits death of central neural cells induced by multiple agents," *Proc. Natl. Acad. Sci. USA*, vol. 90, pp. 4533–4537, May 1993.

Gurney et al., "Motor Neuron Degeneration in Mice That Express a Human Cu,Zn Superoxide Dismutase Mutation," *Science*, vol. 264, pp. 1772–1775, 17 Jun. 1994.

Borchelt et al., "Superoxide dismutase 1 with mutations linked to familial amyotrohic lateral sclerosis possesses significant activity," *Proc. Natl. Acad. Sci. USA*, vol. 91, pp. 8292–8296, Aug. 1994.

Rabizadeh, S., "Mutations associated with amyotrophic lateral sclerosis convert superoxide dismutase from an anti-apoptotic gene to a proapoptoitic gene: Studies in yeast and neural cells," *Proc. Natl. Acad. Sci. USA*, vol. 92, pp. 3024–3028, Mar. 1995.

Nishida et al. "Characterization of three yeast copper–zinc superoxide dismutase mutatns analogous to those coded for in familial amyotrophic lateral sclerosis" *Pro. Natl. Acad. Sci. USA*. 91:9906–9910 (1994).

Pardo et al. "Superoxide dismutase is an abundant component in cell bodies, dendrites, and axons of motor neurons and in a subset of other neurons" *Proc. Natl. Acad. Sci. USA* 92: 954–958 (1995).

Misra. "Reaction of Copper–Zinc Superoxide Dismutase with Diethyldithiocarbamate" *The Journal of Biological Chemistry* 254 No. 22:11623–11628 (1979).

Collard et al. "Defective axonal transport in a transgenic mouse model of amyotrophic lateral sclerosis" *Nature* 375:61–64 (1995).

Yim et al. "Enzyme Function of Copper, Zinc Superoxide Dismutase as a Free Radical Generator" *The Journal of Biological Chemistry* 268 No. 6:4099–4105 (1993).

Conradi, et al., "Long–tme penicallamine–treatment in amyotrophic lateral sclerosis with parallel determination of lead in blood, plasma and urine", Acta Neurol. Scandinav., vol. 65, pp. 203–211, 1983.

Deng et al., "Two novel SOD1 mutations in patients with familial amyotrophic lateral sclerosis", Human Molecular Genetics, vol. 4, No. 6, pp. 1113–1116, 1995.

*Primary Examiner*—Michael P. Woodward
*Assistant Examiner*—Brenda G. Brumback
*Attorney, Agent, or Firm*—Stephen E. Reiter; Gray Cary Ware & Freidenrich; Gregory P. Raymer

[57] ABSTRACT

Familial amyotrophic lateral sclerosis (FALS)-associated mutant CuZnSODs, A4V and G93A, have been discovered to catalyze the generation of hydroxyl radical from hydrogen peroxide at higher rates than that of wild type CuZnSOD. The copper chelator diethyldithiocarbamate (DDC) has been found to inhibit both radical generation and SOD activity of mutant CuZnSODs A4V and G93A at DDC concentrations significantly lower than those required to inhibit wild type CuZnSOD enzyme. In a neural cell culture model of FALS, DDC reverses the effect of four FALS-associated mutants, but does not alter the survival of cells expressing only wild type CuZnSOD. Thus, radical formation may be modulated and ALS treated in subjects with a mutant CuZnSOD enzyme by the administration of copper chelating agents. Treatment can also be affected by the administration of radical scavenging agents, or the administration of expression inhibitors specific for the mutant genes.

20 Claims, 7 Drawing Sheets

10 Gauss

10 Gauss

|  | WT | A4V | G93A |
|---|---|---|---|
| FIG. 3A |  |  |  |
| FIG. 3B |  |  |  |
| FIG. 3C |  |  |  |

10 Gauss

METHOD OF MODULATING RADICAL FORMATION BY MUTANT CUZNSOD ENZYMES

FIELD OF THE INVENTION

The present invention relates to methods for modulating radical formation and treating a subject with amyotrophic lateral sclerosis (ALS; Lou Gehrig's disease). In a particular aspect, the invention relates to methods of treating subjects with a mutant copper-zinc superoxide dismutase (CuZnSOD) protein. Invention treatment involves administration of a copper chelating agent to prevent or reduce the ability of the mutant CuZnSOD protein to generate hydroxyl radicals, or to decrease the peroxidase activity of the mutant CuZnSOD protein. Alternatively, invention treatment can be accomplished by administration of a radical scavenging agent to scavenge the hydroxyl radicals formed by the mutant CuZnSOD protein. In a further aspect, the invention relates to methods of treating a subject having DNA encoding a mutant CuZnSOD protein by administration of an agent to inhibit the expression of such DNA.

BACKGROUND OF THE INVENTION

ALS is a motor neuron degenerative disease that affects approximately one person in ten thousand. About 10–15% of cases are familial (R. H. Brown, Jr., *Cell* 80:687 (1995)), and 20–25% of familial ALS (FALS) cases are associated with dominantly inherited mutations in sod1, the gene that encodes human CuZnSOD (D. R. Rosen, et al., *Nature* 362:59 (1993)). Initial studies of the FALS-associated CuZnSOD mutants demonstrated reduced enzymatic activity (H. X. Deng, et al., *Science* 261:1047 (1993)). However, subsequent studies in a transgenic mouse model (M. E. Gurney, et al., *Science* 264:1772 (1994); M. E. Ripps, et al., *Proc. Natl. Acad. Sci. U.S.A.* 92:689 (1995); C. A. Pardo, et al., *Proc. Natl. Acad. Sci. U.S.A.* 92:954 (1995)) and a cell culture model (S. Rabizadeh, et al., *Proc. Natl. Acad. Sci. U.S.A.* 92:3024 (1995)) of FALS have pointed to a dominant, gain-of-function effect of the FALS-associated CuZnSOD mutants. Neural cell death is observed in these model systems despite the fact that mutant CuZnSODs are expressed in addition to the normal expression of human wild type CuZnSOD. Furthermore, yeast sod 1 null mutants are rescued by FALS-associated mutant human CuZnSOD as efficiently as by wild type CuZnSOD, indicating a high level of enzymatic activity by the mutant proteins (Rabizadeh (1995), supra). Although results from these studies support the existence of a dominant, gain-of-function effect of the mutants, the nature of the function gained remains undetermined (Brown, (1995); J. D. Rothstein, et al., *New Engl. J. Med.* 326:1464 (1992); S. H. Appel, et al, *Eur. J. Neurol. Sci.* 118:169 (1993); J. S. Beckman, et al., *Nature* 364:584 (1993); and J. F. Collard, et al., *Nature* 375:61 (1995)).

CuZnSOD is a homodimeric enzyme containing one copper and one zinc ion per subunit. It is a major antioxidant enzyme, found in virtually all eukaryotic cells. CuZnSOD catalyzes the disproportionation of superoxide to $O_2$ and $H_2O_2$ (J. M. McCord and I. Fridovich, *J. Biol. Chem.* 244:6049 (1969); and I. Fridovich, *Ann. Rev. Biochem.* 64:97 (1995)). In 1975, Hodgson and Fridovich reported that CuZnSOD could be inactivated by $H_2O_2$, and suggested that the mechanism for this inactivation was oxidative inactivation of active site histidine residues (*Biochem.* 14:5294 (1975); *Biochem.* 14:5299 (1975)). They observed further that some but not all hydroxyl radical trapping reagents could protect the enzyme from inactivation by $H_2O_2$ (Id.). In 1989, Cabelli et al., (See, *J. Biol. Chem.* 264:9967 (1989)) concluded that the reaction of $H_2O_2$ with CuZnSOD proceeds by a series of steps, starting with reduction of the oxidized ($Cu^{II}$) form of the enzyme (step 1, below). This is followed by the reaction of $HO_2^-$ with the reduced ($Cu^{I}$) form, in a Fenton-like reaction, to produce hydroxyl radical (step 2, below). Hydroxyl radical produced in step 2 can be scavenged by small anionic scavengers such as formate (step 3 below, where $X^-$ is a Scavenger).

(1)

(2)

(3)

In addition to its activity as a SOD, CuZnSOD catalyzes oxidation of substrates by $H_2O_2$ at rates competitive with its own oxidative inactivation by the same reagent (Hodgson and Fridovich, (1975), supra (both articles), and Cabelli, (1989), supra). A convenient substrate used to study this type of reaction is the spin trapping agent 5,5'-dimethyl-1-pyrroline N-oxide (DMPO), which reacts with $H_2O_2$ to give its electron paramagnetic resonance (EPR)-detectable hydroxyl adduct, DMPO-OH.

In 1990, it was demonstrated that hydroxyl radicals are generated in the reaction of $H_2O_2$ with CuZnSOD (M. B. Yim, et al., *Proc. Natl. Acad. Sci. U.S.A.* 87:5006 (1990)). Three distinct fates for the hydroxyl radicals were described (Hodgson and Fridovich, (1975), supra (both articles); Yim, et al., (1990), supra; and M. B. Yim, et al., *J. Biol. Chem.* 268:4099 (1993)). First, the hydroxyl radicals could react directly with CuZnSOD, irreversibly inactivating the enzyme. Second, the hydroxyl radicals could exit from the active site channel, causing oxidative damage to other molecules within the short range of hydroxyl radical diffusion. Third, the radicals could be scavenged by small anionic molecules (e.g., formate or glutamate) capable of entering the active site channel. Although such a reaction would prevent damage to CuZnSOD, thereby prolonging the enzyme's half-life, the resulting scavenger radicals (e.g., formyl or glutamyl radicals) could potentially diffuse away from the enzyme and interact with targets beyond the range of hydroxyl radical diffusion (Yim, et al., (1993), supra). Based upon this evidence, it has not been possible to establish whether the function gained in FALS-associated CuZnSOD mutants is best described as an increase in the generation of hydroxyl radicals, or an increase in peroxidase activity. Therefore, reference to either activity, throughout this specification, is meant to encompass either possibility.

Thus, it remains to be determined what is the cause of hydroxyl radical production by CuZnSOD, and what effect it has on cellular biochemistry. It also remains to be determined whether there is any connection between ALS and hydroxyl radical production by (or increased peroxidase activity of) CuZnSOD. Therefore, it remains to be discovered what can be done to modulate hydroxyl radical production by CuZnSOD, and thereby treat ALS.

BRIEF DESCRIPTION OF THE INVENTION

FALS-associated mutant CuZnSODs, A4V and G93A, have been discovered to catalyze the oxidation of substrates using hydrogen peroxide (peroxidase activity) at higher rates than that of wild type CuZnSOD. The copper chelator diethyldithiocarbamate (DDC) has been found to inhibit this activity in the mutant CuZnSODs A4V and G93A at concentrations significantly lower than required for DDC to inhibit wild type CuZnSOD. In a neural cell culture model of FALS, DDC reverses the effect of four FALS-associated mutants, but does not alter the survival of cells expressing only wild type CuZnSOD.

This invention demonstrates that ALS caused by mutant CuZnSODs is treatable. Thus, copper chelating agents are shown to be capable of inhibiting the hydroxyl radical forming activities of mutant CuZnSOD enzymes at levels that do not have a significant effect on the SOD activity of the mutant or wild type enzyme. Thus the beneficial actions of the enzyme may be preserved while treating the harmful, disease-causing actions.

BRIEF DESCRIPTION OF THE FIGURES

FIG. 1(A)–(D) illustrate the EPR spectra of the DMPO-OH adduct formed by fully metallated wild type and mutant CuZnSODs, and by copper ions. FIG. 1(A) was generated using 1.25 μM wild type CuZnSOD; FIG. 1(B) was generated using 1.25 μM CuZnSOD mutant A4V; FIG. 1(C) was generated using 1.25 μM CuZnSOD mutant G93A; and FIG. 1(D) was generated using 2.5 μM $CuSO_4$.

FIG. 2(A)–(E) illustrate the EPR spectra of the DMPO-OH adduct formed by wild type CuZnSOD and mutant A4V with varying degrees of copper metallation of the proteins. FIG. 2(A) was generated using copper-free enzyme; FIG. 2(B) was generated using 25% copper metallated; FIG. 2(C) was generated using 50% copper metallated; FIG. 2(D) was generated using 75% copper metallated; and FIG. 2(E) was generated using 100% copper metallated.

FIG. 3(A)–(C) illustrate the EPR spectra of the DMPO-OH adducts formed by wild type, A4V, and G93A CuZnSOD with varying concentrations of DDC. FIG. 3(A) was generated with no DDC added; FIG. 3(B) was generated with 0.62 μM DDC (0.25 equivalents per enzyme subunit copper); and FIG. 3(C) was generated with 10 μM DDC (4.0 equivalents per enzyme subunit copper).

FIG. 4(A)–(B) illustrates the concentrations of DMPO-OH adducts formed during the reaction of $H_2O_2$ (30 μ) with wild type, A4V, and G93A CuZnSOD with varying concentrations of DDC. FIG. 4(A) shows two trials with wild type CuZnSOD; and FIG. 4(B) shows the mutant CuZnSOD results. Filled circles and filled squares: wild type CuZnSOD, two separate experiments; open triangles: CuZnSOD mutant G37R; open circles: CuZnSOD mutant A4V.

DETAILED DESCRIPTION OF THE INVENTION

In accordance with the present invention, there are provided methods of treating a subject with ALS (or a subject susceptible to developing ALS) by administering to said subject an amount of a copper chelating agent effective to ameliorate the symptoms of ALS.

In another embodiment, there are provided methods of treating a subject having a mutant sod1 gene by inhibiting peroxidase activity of said mutant sod1 gene.

In yet another embodiment, there are provided methods of treating a subject having a mutant CuZnSOD protein by administering to said subject a radical scavenging agent in an amount effective to scavenge radicals formed by said mutant CuZnSOD protein.

In still another embodiment, there are provided methods of modulating radical formation in a subject having a mutant CuZnSOD protein by administering to said subject a copper chelating agent in an amount effective to modulate radical formation by said mutant CuZnSOD protein.

In a further embodiment, there are provided methods of modulating radical formation in cells having a mutant CuZnSOD protein by administering to said cells a copper chelating agent in an amount effective to modulate radical formation by said mutant CuZnSOD protein.

In a still further embodiment, there are provided methods of treating a subject having DNA encoding a mutant sod1 gene by administering to said subject an inhibitor in an amount effective to inhibit expression of said DNA encoding a mutant sod 1 gene.

The present invention is based on the hypothesis that the FALS-associated mutant CuZnSODs might enhance the catalytic generation of radicals from $H_2O_2$ or the peroxidase activity of the enzyme. First, in a cell culture model of FALS, mutant human CuZnSODs (A4V, G37R) increase apoptosis (programmed cell death), whereas the wild type CuZnSOD inhibits apoptosis (Rabizadeh (1995); and L. J. S. Greenlund, et al., *Neuron* 14:303 (1995)). Apoptosis in many paradigms is mediated by reactive oxygen species (T. A. Sarafian and D. E. Bredesen, *Free Radic. Res.* 21:1 (1994)). Second, analysis of the locations of the FALS-associated CuZnSOD mutations (Deng (1993), supra) suggests the possibility of more open CuZnSOD structures, which could conceivably allow greater access of radical-forming reactants to the active site copper. Third, it has been observed in cell culture that ALS mutant CuZnSODs have reduced half-lives in comparison to wild type CuZnSOD (D. R. Borchelt, et al., *Proc. Natl. Acad. Sci. U.S.A.* 270:3234 (1994)). This finding is compatible with enhanced enzyme damage due to hydroxyl radical generation (although it is equally compatible with enhanced proteolysis due to an alteration in enzyme structure).

In order to test the hypothesis that FALS-associated mutations augment peroxidase activity, recombinant wild type CuZnSOD and mutant CuZnSOD A4V (indicates that the valine at amino acid residue 4 in the enzyme has been replaced with an alanine) and G93A (alanine at position 93 was replaced with glycine) DNA constructs were expressed in *Saccharomyces cerevisiae*, and the expressed proteins purified to homogeneity (McCord and Fridovich (1969), supra) (for details, see Example 6). Copper and zinc were removed by repeated dialysis, as described previously (C. R. Nishid, et al., *Proc. Natl. Acad. Sci. U.S.A.* 91:9906 (1994)), and the apoenzymes were then remetallated by the gradual addition of $CuSO_4$ (Y. Lu, et al., *J. Am. Chem. Soc.* 115:5907 (1993)). The degree of metallation was confirmed using atomic absorption. EPR studies were then performed, using DMPO (Yim (1993), supra).

In the presence of $H_2O_2$ and DMPO, the fully metallated mutant and wild type CuZnSOD enzymes all produced the quadruplet signal characteristic of the hydroxyl radical adduct DMPO-OH (FIG. 1(A)–(D)). Double integration of the signals from the adduct demonstrated that higher concentrations of hydroxyl radical were trapped in the case of the FALS-associated mutant enzymes. For example, the signal from CuZnSOD mutant A4V was 3.0±1.1 times the wild type CuZnSOD signal (n=10; p<0.0005 by unpaired two-tailed t-test; range=2.1–5.7 times the wild type CuZnSOD signal); and from CuZnSOD mutant G93A, 2.1±0.3 times the wild type CuZnSOD signal (n=5; p<0.025 by unpaired two-tailed t-test; range=1.8–2.6 times the wild type CuZnSOD signal). The amplitude of the signal generated by the CuZnSOD mutant A4V was reproducibly greater than that from the CuZnSOD mutant G93A, which was, in turn reproducibly greater than that from wild type CuZnSOD.

Figure 1A:
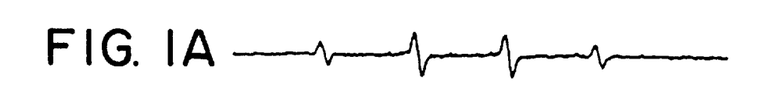
Figure 1B:
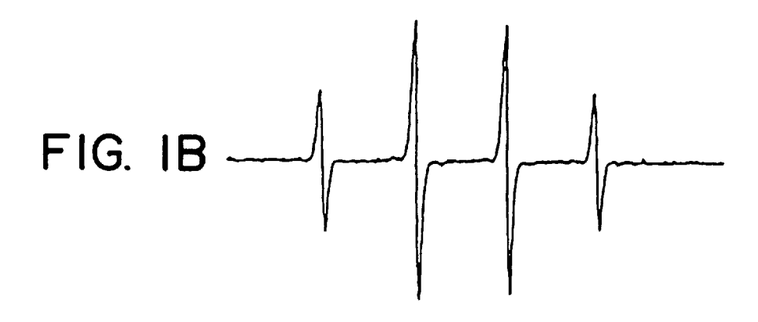
Figure 1C:
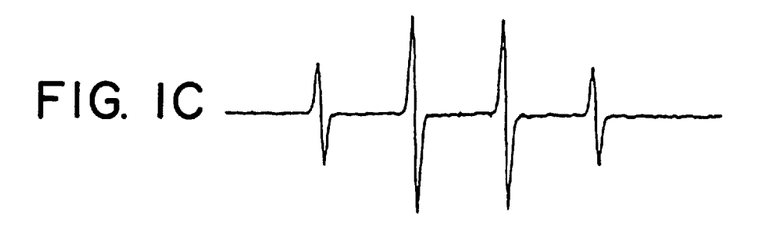
Figure 1D:
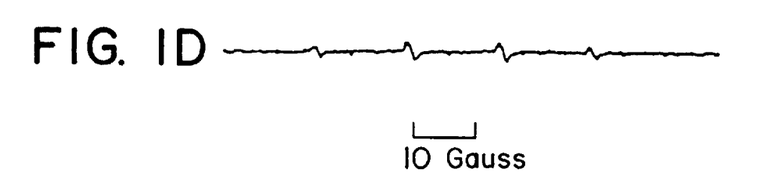
Figures 2A, 2B:
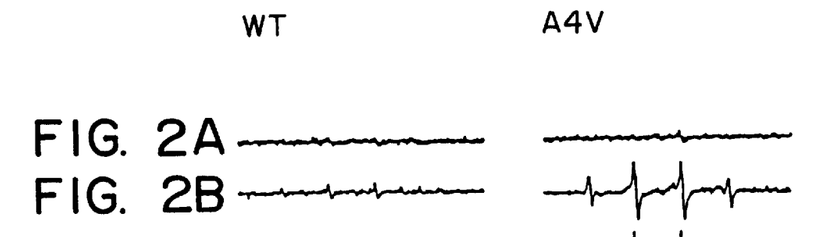
Figures 2C, 2D:
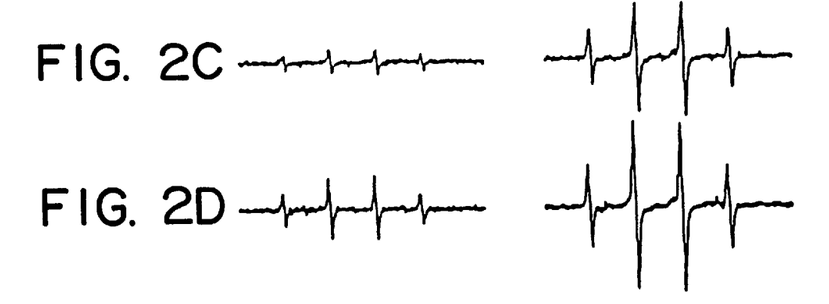
Figure 2E:
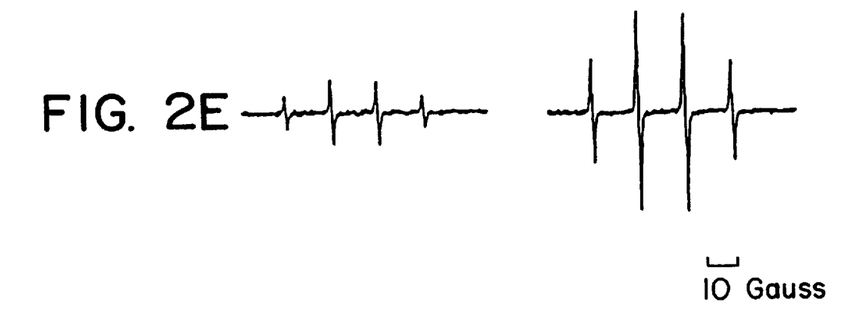

The apoenzymes, by contrast, did not produce hydroxyl radicals detectable by EPR (FIG. 2(A)). With increasing degrees of metallation, the enzymes gave increasing DMPO-OH specific EPR signals due to hydroxyl radical production (FIG. 2(B)–(E)). Differences between wild type and mutant enzymes were seen at all degrees of metallation. The increase in the EPR signals was not simply due to free copper in solution, since free $Cu^{2+}$ without any enzyme does not give a significant EPR signal (FIG. 1(D)). Neither could the spectra be explained simply by the preferential loss of zinc from the mutant CuZnSODs, since the zinc-free derivatives of wild type CuZnSODs gave results similar to the fully metallated wild type enzyme.

Previous studies of the reaction of wild type CuZnSOD with $H_2O_2$ suggested strongly that the reaction occurs at the active site of the enzyme, i.e., at the copper ion bound to each subunit. It was predicted, therefore, that the reaction would be inhibited by a copper-ion chelating agent that would either bind to or remove the copper from the active site of the protein. Diethyldithiocarbamate (DDC) is a chelator capable of first binding to and then removing copper ions from CuZnSOD at physiological pH, and it has been shown to inhibit the SOD activity of CuZnSOD both in vitro and in vivo (H. P. Misra, *J. Biol. Chem.* 264:11623 (1979))

Figure 4A:
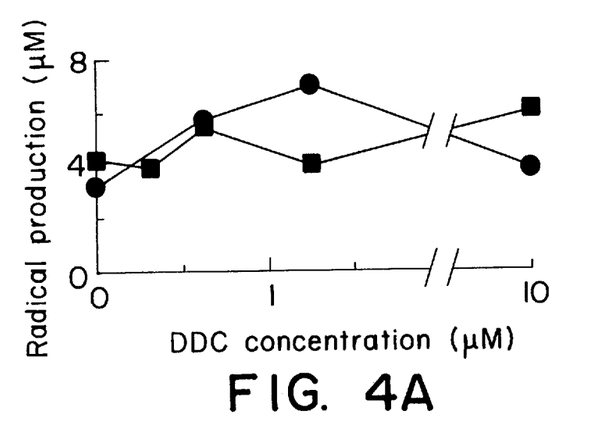
Figure 4B:
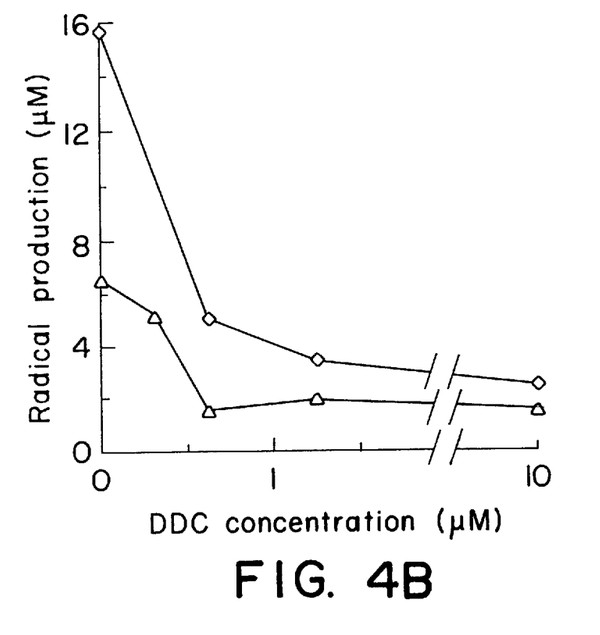
Figure 5:
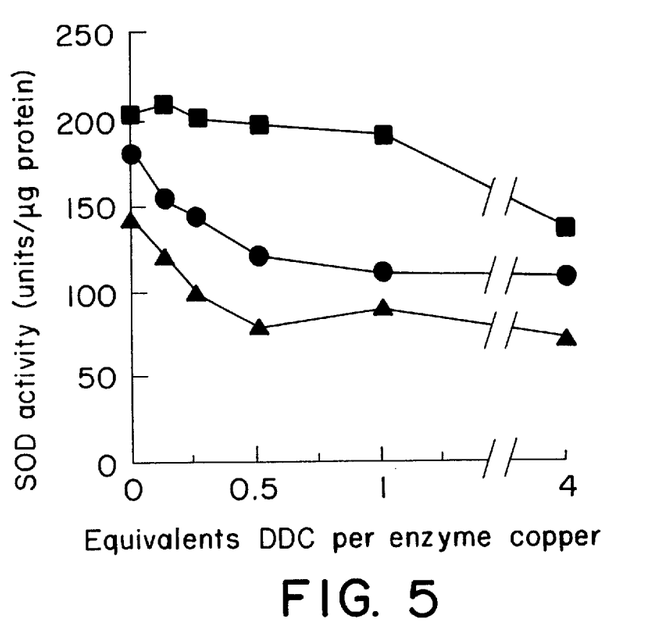
FIG. 5 illustrates the superoxide dismutase activity of purified wild type CuZnSOD and mutant CuZnSOD enzymes A4V and G93A with varying concentrations of DDC. Filled squares: wild type CuZnSOD; filled circles: CuZnSOD mutant G37R; filled triangles: CuZnSOD mutant A4V.

Therefore, the effect of adding DDC to wild type CuZnSOD, mutant CuZnSOD A4V, and mutant CuZnSOD G93A was studied. A fundamental difference in the copper reactivity of the mutant enzymes in comparison to the wild type enzyme was demonstrated by their disparate responses. Whereas the wild type CuZnSOD showed a concentration-dependent increase in peroxidase activity following the addition of DDC, both mutant CuZnSOD A4V and mutant CuZnSOD G93A showed a progressive decrease in peroxidase activity with increasing concentrations of DDC (FIG. 3(A)–(C) and FIG. 4(A)–(B)). Furthermore, it was found that equimolar DDC (relative to enzyme subunit copper) had no effect on wild type CuZnSOD enzymatic activity, as reported previously (Misra (1979), supra), while the activity of both mutant CuZnSODs was inhibited even when only 0.25 equivalents of DDC per copper were added (FIG. 5).

Figure 6:
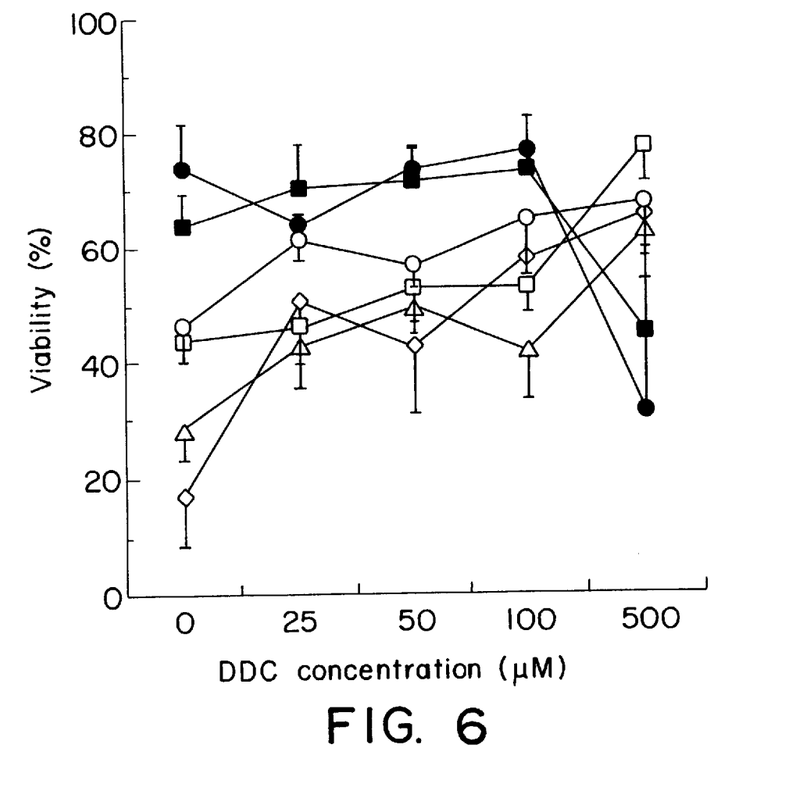
FIG. 6 illustrates the viability of CSM 14.1 cells expressing wild type and mutant CuZnSODs, with increasing concentrations of DDC added to the growth media. Filled circles: wild type CuZnSOD; filled squares: control (vector only); open diamonds: CuZnSOD mutant G37R; open triangles: CuZnSOD mutant A4V; open squares: CuZnSOD mutant G41D; open circles: CuZnSOD mutant G85R. Error bars represent standard error.
Figure 7:
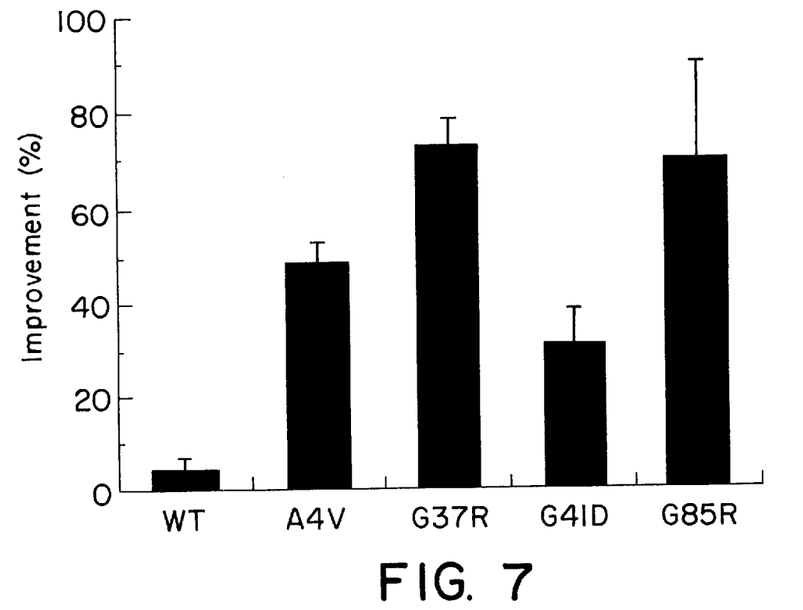
FIG. 7 illustrates the cellular viability shown in FIG. 6, expressed as percent improvement in survival relative to control transfectants, with a DDC concentration of 100 μM.

It was reasonable to postulate that if the peroxidase activity was important in SOD-associated FALS and was inhibited by DDC, then a low concentration of DDC would inhibit the process of neural degeneration associated with the expression of mutant CuZnSODs. The effect of adding DDC to a neural cell culture model of FALS, in which overexpression of the wild type CuZnSOD inhibits apoptosis while similar levels of expression of FALS-associated mutant CuZnSODs enhance apoptosis (Rabizadeh (1995), supra), was therefore investigated. The conditionally-immortalized rat nigral neural cell line CSM 14.1 (M. Durand, et al., *Soc. Neurosci. Abs.* 16:40 (1990); and L. T. Zhong, et al., *Proc. Natl. Acad. Sci. U.S.A.* 90:4533 (1993)) was transfected with vectors carrying wild type CuZnSOD or the mutant CuZnSODs A4V, G37R, G41D, or G85R. As had been observed previously (Rabizadeh (1995), supra), overexpression of the wild type CuZnSOD inhibited apoptosis induced in the cells by serum withdrawal, whereas all four mutant CuZnSODs tested were found to enhance apoptosis over the control. DDC (25–100 $\mu$M) added to the cultures inhibited apoptosis induced by all four mutant CuZnSODs from 30–70%, but had no effect on cells overexpressing wild type CuZnSOD (FIGS. 6 and 7). DDC at a concentration of 500 $\mu$M decreased the viability of the cells expressing wild type CuZnSOD but continued to rescue the cells expressing the mutant CuZnSODs. DDC at a concentration of 1 mM or greater was toxic in all groups.

Thus, one aspect of the invention is the modulation of radical formation and the treatment of ALS by administration to a subject of a copper chelating agent in a pharmaceutically acceptable vehicle. Classes of copper chelating agents contemplated for use in the practice of the present invention include in particular those with access to the active site channel of mutant CuZnSOD. Particular copper chelating agents contemplated for use in the practice of the present invention include DDC, penicillamine, catechol, diethylenetriaminepentaacetic acid, diisopropylsalicylate, dithizone, ethylenediaminetetraacetic acid, tetraethylenepentamine, triethylenetetramine, tetrakis-2-(pyridylmethyl) ethylenediamine, and the like.

A presently preferred copper chelating agent contemplated for use in the practice of the present invention is DDC. DDC is preferably used to treat a subject by administration of about 0.001 to about 1 g of DDC per kg body weight of the subject. Of course, The required dosage will vary with the severity of the condition and with the duration of desired treatment, and this should be determined by and administered under the guidance of a physician. In a presently preferred embodiment, 0.1 g of DDC per kg body weight is administered to the subject. More important than the amount administered to a subject is the concentration of the DDC that is achieved in the subject's neural cells. The optimal intracellular concentration of DDC is relatively the same as the intracellular concentration of the CuZnSOD enzyme. Thus, the preferred intracellular concentration is in the range of about 0.01 to about 1 $\mu$M. Preferably, a sufficient amount of DDC is administered so as to achieve an extracellular DDC concentration in the range of about 10 to about 500 $\mu$M. In a presently preferred embodiment, the extracellular DDC concentration will be about 100 $\mu$M.

When penicillamine is used, it is preferably administered in an amount of about 0.001 to about 1 g of penicillamine per kg body weight of the subject. In a presently preferred embodiment, 0.1 g of penicillamine per kg body weight is administered to the subject. More important than the amount administered to a subject is the concentration of the penicillamine that is achieved in the subject's neural cells. The optimal intracellular concentration of penicillamine is relatively the same as the intracellular concentration of the CuZnSOD enzyme. Thus, the preferred intracellular concentration is in the range of about 0.01 to about 1 $\mu$M penicillamine. Preferably, a sufficient amount of penicillamine is administered so as to achieve an extracellular penicillamine concentration in the range of about 10 to about 500 $\mu$M. In a presently preferred embodiment, the extracellular penicillamine concentration will be about 100 $\mu$M.

Another aspect of the invention is the modulation of radical formation and the treatment of ALS by administration to a subject of a radical scavenging agent in a pharmaceutically acceptable vehicle. Classes of radical scavenging agents include thiol reagents, lipid-soluble antioxidants, water-soluble antioxidants, spin-trapping agents, and the like. Particular radical scavenging agents contemplated for use in the invention include DMPO, tocopherol, ascorbate, N-acetylcysteine, N-t-α-phenylnitrone, and the like.

A presently preferred radical scavenging agent is DMPO. DMPO is preferably used to treat a subject by administration of about 0.001 to about 1 g of DMPO per kg body weight of the subject. In a presently preferred embodiment, 0.01 g of DMPO per kg body weight is administered to the subject. More important than the amount administered to a subject is the concentration of the DMPO that is achieved in the subject's neural cells. Preferably, a sufficient amount of DMPO is administered so as to achieve a cellular DMPO concentration in the range of about 10 to about 1000 $\mu$M. In a presently preferred embodiment, the cellular DMPO concentration will be about 45 $\mu$M.

It has been shown that ALS caused by mutant sod1 genes may be inherited in a dominant manner. Thus, afflicted subjects may have both a wild type and a mutant version of the gene within their genome. In these subjects, if the expression of the mutant gene could be inhibited, the disease state would be reduced or abated, while the wild type gene could express a sufficient amount of the active, wild type enzyme to provide the SOD activity required by the patient.

Therefore, another aspect of the invention is the modulation of radical formation and the treatment of ALS by administration to a subject of an expression inhibitor in an amount effective to inhibit expression of the DNA encoding the mutant sod 1 protein. A variety of methods to achieve this aim will be apparent to those of ordinary skill in the art, including the use of antisense DNA or RNA, the use of retroviral constructs that will integrate specifically into the mutant gene to prevent expression thereof, adenoviral vectors, and the like.

Many mutant sod1 genes have been elucidated, including A4V, G93A, G37R, G41D, G85R, I112T, I113T, D90A, E100, L106, V148, H43, H46R, L38V, L144, and the like. Of these, A4V is known to be involved in a particularly severe form of ALS, and therefore may be the most suited to treatment by the invention methods.

Figure 3A:
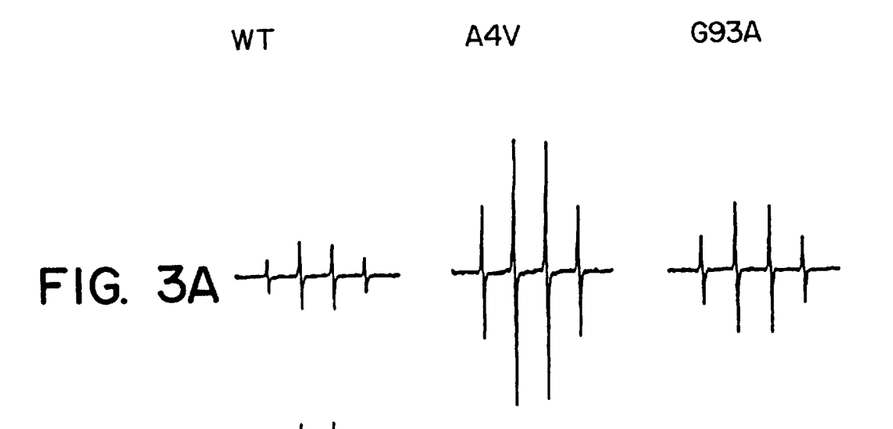
Figure 3B:
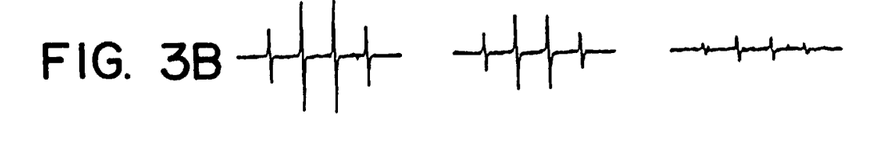
Figure 3C:
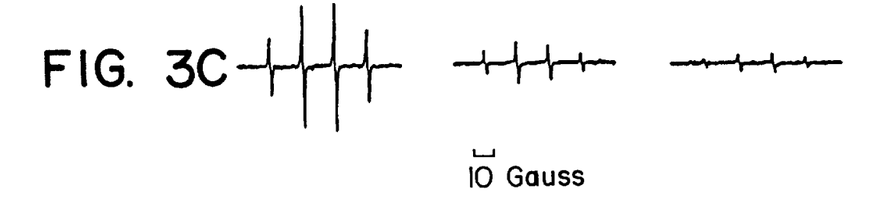

The results of the work done in developing the invention demonstrate a qualitatively different chemistry for the active site copper of the CuZnSOD mutants A4V and G93A as compared to the wild type enzyme. The alteration in reactivity of the CuZnSOD mutants A4V and G93A relative to the wild type CuZnSOD enzyme is demonstrated by their responses to the chelating agent DDC. Whereas hydroxyl radical generation by the wild type CuZnSOD is slightly enhanced by stoichiometric amounts of DDC, similar amounts markedly reduce hydroxyl radical generation by the mutants (FIGS. 3 and 4). Additionally, wild type CuZnSOD shows no loss of SOD activity at concentrations of DDC that cause substantial reduction of the SOD activity of CuZnSOD mutants A4V and G93A (FIG. 5). Results both from previous studies (Yim (1990), supra) and the present invention show that hydroxyl radical generation requires an active CuZnSOD; neither apoenzyme nor boiled, inactivated enzyme demonstrates the effect. Furthermore, the enhancement of hydroxyl radical generation by the CuZnSOD mutants A4V and G93A is not mimicked by zinc-free derivatives of wild type CuZnSOD nor by adding free copper to the solution. Thus, the enhancement of hydroxyl radical generation by the CuZnSOD mutants A4V and G93A is due to the reactivity of copper within the active site of CuZnSOD.

Any model that explains mutant CuZnSOD-associated FALS satisfactorily must account for the dominant inheritance pattern, the fact that different CuZnSOD mutations cause the same disease, and the differing degrees of severity of the disease caused by different mutations. The enhanced production of hydroxyl radicals by FALS-associated CuZnSOD mutants A4V and G93A is an effect that is compatible with the required characteristics of the mutants for the initiation of motor neuron loss in FALS. First, the effect is a gain-of-function effect, and could account for the dominant inheritance pattern. Second, multiple FALS-associated mutants demonstrate the effect. Third, it is compatible with the finding that FALS-associated CuZnSOD mutants induce apoptosis in cultured neural cells, whereas the wild type CuZnSOD has an anti-apoptotic effect (Rabizadeh (1995); Greenlund et al. (1995); and D. E. Bredesen, Apoptosis II: *The Molecular Basis of Apoptosis in Disease* (Cold Spring Harbor Laboratory Press, 1994) pp. 397–421). Fourth, the effect is compatible with the finding that copper chelation inhibits the pro-apoptotic effect of the mutants A4V, G37R, G41D, and G85R, yet does not affect apoptosis in cells overexpressing wild type CuZnSOD. Finally, the effect is more pronounced for the CuZnSOD mutant A4V than for the CuZnSOD mutant G93A, and A4V is associated with a particularly severe form of FALS (D. R. Rosen, et al., *Hum. Mol. Genet.* 3:981 (1994)).

Despite the demonstration that peroxidase activity is enhanced by the FALS-associated mutations, it is unlikely that free hydroxyl radical is itself the predominant damaging species produced (Yim (1993), supra). Free hydroxyl radicals react at diffusion-controlled rates and are therefore likely to be scavenged by small-molecule antioxidants immediately after they are produced in vivo. It is more likely that a small, anionic substrate(s), such as formate or glutamate, scavenges the hydroxyl radical within the active site channel, forming free radical products such as formyl or glutamyl radicals, which in turn may participate in more long range oxidative reactions. In fact, the ability of glutamate to prevent the inhibition of wild type CuZnSOD by reaction with $H_2O_2$ has been attributed to such a reaction (Id.). The present data indicate that this mode of free radical production is substantially enhanced by the FALS-associated CuZnSOD mutants A4V and G93A.

Motor neurons have been reported to have particularly high levels of CuZnSOD, implying that this cell type may require a high rate of superoxide dismutation. Indeed, this notion has been supported by the finding of relatively restricted motor neuron apoptosis in response to CuZnSOD inhibition in organotypic cultures (J. D. Rothstein, et al., *Proc. Natl. Acad. Sci. U.S.A.* 91:4155 (1994)). Although many of the FALS-associated CuZnSOD mutants retain the ability to dismutate superoxide enzymatically, at least CuZnSOD mutants A4V and G93A also demonstrate a high rate of hydroxyl radical generation. Thus, the requirement for high-level expression of CuZnSOD may place motor neurons at high risk for damage by these mutants. The observation that there are other neurons that express sod1 at high levels but do not degenerate in FALS (C. A. Pardo, et al., *Proc. Natl. Acad. Sci. U.S.A.* 92:954 (1995)) might conceivably be explained by a difference in the availability of substrate ($H_2O_2$), scavengers (e.g., glutamate), or targets (e.g., glutamate transporters).

The results of the DDC experiments described herein do not discriminate between the possibility that DDC causes removal of copper from the active site of the mutant enzymes, and the alternate possibility that Cu-DDC remains in the active site. Nonetheless, results from Misra (1979, supra) indicate that binding of DDC to wild type bovine CuZnSOD does not cause an inhibition of SOD activity until sufficient DDC is present to cause removal of copper from the active site. It is likely therefore that the inhibition of the SOD activity of A4V and G93A by DDC is due to copper ion removal from the protein. Thus CuZnSOD mutants A4V and G93A may have a lower affinity than wild type CuZnSOD for copper ions in the active site, in addition to their enhanced ability to catalyze free radical production by hydrogen peroxide.

The finding that copper chelation with DDC, at a concentration that does not decrease wild type SOD enzymatic activity, reduces both hydroxyl radical generation and the pro-apoptotic effects of CuZnSOD mutants, indicates that the use of copper chelators will prove beneficial in animal models of FALS (Gurney (1994), supra; Ripps (1995), supra; and Pardo (1995), supra), and in the treatment of patients with FALS-associated sod1 mutations.

The invention will now be described in greater detail with reference to the following non-limiting examples.

EXAMPLES

Example 1

Hydroxyl radical formation by mutant and wild type CuZnSODs was determined by measuring the amount of adduct formed when the radical scavenging agent 5,5'-dimethyl-1-pyrroline N-oxide (DMPO) was added to the hydroxyl radical forming reaction. The amount of the DMPO-OH radical adduct formed was determined by measurement of the unique EPR spectra signals of the adduct.

Reactions were carried out as described (Yim (1990), supra), with minor modifications. Reaction mixes consisted of 1.25 $\mu$M protein (or 2.5 $\mu$M CuSO$_4$), 45 mM DMPO (Aldrich) in 23.5 mM NaHCO$_3$ buffer (pH 7.4) balanced with 5% CO$_2$/95% N$_2$ gas. 30 mM hydrogen peroxide was injected to start the reaction. Spectra developed after 30 to 45 seconds, were recorded at 5 minutes, and were stable for more than 30 minutes. EPR spectra were recorded on a Bruker ER 200 D at room temperature, operated at 9.5 GHz with a modulation frequency of 100 KHz. Conditions were: microwave power 20.7 milliwatts, modulation amplitude 1 Gauss (G), time constant 10 ms, sweep width 100 G with 2046 point resolution.

The samples were prepared and handled, and all measurements executed, in a strictly oxygen-free atmosphere, to prevent radical scavenging by molecular oxygen. Buffers were treated with Chelex 100 (Biorad) to eliminate the possibility of contamination by trace metals. DMPO was purified by filtration with neutral decolorizing charcoal (Aldrich) (G. H. Buettner and L. W. Oberley, *Biochem. Biophys. Res. Comm.* 83:69 (1978)). The concentration of DMPO was calibrated spectrophotometrically, using an extinction coefficient $\Sigma_{226}$=7.22×10$^3$ M$^{-1}$ cm$^{-1}$ (E. Finkelstein, et al., *Arch. Bioch. Biophys.* 200:1 (1980)). An aqueous flat cell (Wilmad) was used to hold the samples. The concentrations of the apoproteins were calculated from the extinction coefficient $\Sigma_{278}$=1.08×10$^4$ M$^{-1}$ cm$^{-1}$.

The signals shown in FIG. 1(A)–(D) are representative; measurements were repeated 5 to 10 times, always paired with the wild type protein. Double integration of these signals using the spin label carbamoyl-proxyl (Aldrich) as a standard to quantitate the hydroxyl radical production showed that wild type CuZnSOD produced 3.2 $\mu$M, CuZnSOD mutant A4V produced 15.6 $\mu$M, CuZnSOD mutant G93A produced 6.5 $\mu$M, and CuSO$_4$ produced 1.9 $\mu$M hydroxyl radical in this experiment.

Example 2

Hydroxyl radical formation by wild type and mutant A4V CuZnSODs was determined with varying degrees of copper metallation of the enzymes. The same methodology was used as in Example 1, with the samples containing 1.25 $\mu$M enzyme, 45 mM DMPO and 30 mM H$_2$O$_2$ in 23.5 mM NaHC$_3$O buffer, pH 7.4. Experiments were repeated three times, and representative signals, recorded at 3 minutes post-initiation, are shown in FIG. 2(A)–(E). The mutant A4V CuZnSOD produced more adduct at all levels of metallation, although neither enzyme produced any measurable adduct when no copper was present.

Example 3

Hydroxyl radical formation was next measured as varying amounts of DDC were added to the reaction. Experiments were performed as described in Example 1, and repeated 2–3 times. DDC was freshly prepared, and added to the CuZnSOD immediately before adding the DMPO and injecting the H$_2$O$_2$. EPR spectra, shown in FIG. 3(A)–(C), were recorded at 2.5 minutes post-initiation. While DDC caused a slight increase in adduct production by wild type CuZnSOD enzyme, a sharp decrease in adduct production is seen in both mutant enzyme samples.

FIG. 4 shows the data of FIG. 3(A)–(C) plotted as hydroxyl radical formation (i.e., adduct concentration) vs. DDC concentration. The calculation of adduct concentrations was as described in Example 1. The upper graph shows two separate experiments with wild type CuZnSOD. In the lower graph, the diamonds represent the CuZnSOD mutant A4V, and the triangles represent the CuZnSOD mutant G93A.

It is seen that 0.25 equivalent concentrations of DDC (0.62 $\mu$M) per enzyme subunit copper reduced the hydroxyl radical production by the CuZnSOD mutants A4V and G93A to 22% and 32%, respectively. The wild type CuZnSOD showed a slight increase in hydroxyl radical generation of 115% compared to the hydroxyl radical production without DDC. Even 4.0 equivalents of DDC per enzyme subunit copper had no negative effect on hydroxyl radical production by the wild type enzyme.

Example 4

Now that it has been shown that addition of DDC to CuZnSOD mutants reduces hydroxyl radical formation, the effect of DDC on the SOD activity of both mutant and wild type CuZnSOD enzymes was tested. DDC was freshly prepared, added to the proteins, and allowed to incubate for 5 minutes prior to measurements. SOD activity was assayed as described previously (Rabizadeh (1995); and R. E. Heikkila and F. Cabbat, *Anal. Bioch.* 75:356 (1976)). While high concentrations of DDC (4 equivalents/enzyme copper) had an impact on all CuZnSODs, lower concentrations of DDC (less than 1 equivalent/enzyme copper) had little effect on the SOD activity of wild type CuZnSOD (See FIG. 5).

Example 5

Next the in vivo efficacy of DDC was tested. Temperature-sensitive nigral neural cells (SCM 14.1) were transfected with wild type and A4V, G37R, G85R, and G41D mutant CuZnSOD constructs by methods described previously (Rabizadeh (1995), supra). Following selection in puromycin (7 $\mu$g/ml), cells were plated onto 96-well plates. DDC was added at concentrations of 25 $\mu$M–1 mM to cells in serum-free media. Viability was assessed at 60 hours, by methods described in Rabizadeh (1995), and is shown in FIG. 6. There was no significant improvement at any DDC concentration for the cells transfected with the wild type CuZnSOD construct. In contrast, all mutants showed highly significant improvements in survival ($p<0.01$ by unpaired, two-tailed t-tests; $n=4$) at 25–500 $\mu$M DDC, except G41D (N.S. at 25 $\mu$M; p 0.25 at 50, 100 $\mu$M; $p<0.01$ at 500 $\mu$M DDC) and G85R ($p<0.05$ at 50 $\mu$M; $p<0.01$ at 25, 100, and 500 $\mu$M DDC).

FIG. 7 illustrates the improvement in viability of the various transfected cell lines when DDC was added at a concentration of 100 $\mu$M, as opposed to viability with no added DDC in the growth media. This was calculated as follows:

$$viability=[Vm(x)-Vm(0)]/[Vc(0)-Vm(0)]$$

where Vm(x) is defined as the viability of mutant transfected cells at x concentration of DDC, Vm(0) is defined as viability of mutant transfected cells at a DDC concentration of 0, and Vc(0) is defined as viability of control transfected cells at a DDC concentration of 0. Standard errors were computed by the delta method for computing the asymptotic standard error for the estimate of a nonlinear function (D. Colquhoun, Lectures on *Biostatistics* (Clarendon Press, 1971) pp. 39–42).

While 100 $\mu$M DDC increased viability of the various mutant transfected cell lines from 30–70%, it had no significant effect on the viability of cell lines transfected with the wild type gene.

Example 6

CuZnSOD enzyme proteins, used in Examples 1–4, were prepared as follows. cDNA clones for wild type CuZnSOD, ALS CuZnSOD mutant A4V, and ALS CuZnSOD mutant G93A, under the control of the yeast CuZnSOD promoter, were cloned into the yeast shuttle vector YEp351, and transformed into yeast strain EG118, which is null for yeast sod1 (Rabizadeh (1995), supra). Cultures of 10 liters were grown in highly aerated, YEPD medium (5% yeast extract, 10% peptone, 2% dextrose) for 24 hours. Cells were harvested by centrifugation, and lysed using an equal volume of 0.5 mm glass beads in a blender. Protein purification was as described previously (Lu (1993), supra) with the addition of a final Sephadex G75 chromatography step. The purified proteins were homogeneous, as indicated by SDS-polyacrylamide gel electrophoresis. For each batch, 50–200 mg of purified protein was obtained. Human CuZnSOD expressed in yeast is properly N-terminal acetylated (R. A. Hallewell, et al., *Bio/Tech.* 5:363 (1987)). The identities of the purified mutant proteins were verified by electrospray mass spectrometry, which detected the change in mass due to single amino acid substitutions. For both wild type and mutant CuZnSOD proteins, the observed and predicted masses corresponded, within 2–4 atomic mass units.

While the invention has been described in detail with reference to certain preferred embodiments thereof, it will be understood that modifications and variations are within the spirit and scope of that which is described and claimed.

That which is claimed is:

1. A method of modulating radical formation in a subject previously determined to have a mutant CuZnSOD protein, said method comprising administering to said subject a copper chelating agent in an amount effective to modulate radical formation by said mutant CuZnSOD protein.

2. The method of claim 1 wherein said copper chelating agent is selected from the group consisting of diethyldithiocarbamate, penicillamine, catechol, diethylenetriaminepentaacetic acid, diisopropylsalicylate, dithizone, ethylenediaminetetraacetic acid, tetraethylenepentamine, triethylenetetramine, and tetrakis-2-(pyridylmethyl) ethylenediamine.

3. The method of claim 1 wherein said copper chelating agent is selected from the group consisting of diethyldithiocarbamate and penicillamine.

4. The method of claim 3 wherein said copper chelating agent is DDC, and said amount is about 0.001 to about 1 g of DDC per kg body weight of said subject.

5. The method of claim 3 wherein said copper chelating agent is DDC, and said amount of DDC yields a DDC concentration in neural cells of said subject of about 0.01 to about 1 :M.

6. The method of claim 3 wherein said copper chelating agent is penicillamine, and said amount is about 0.001 to about 1 g of penicillamine per kg body weight of said subject.

7. The method of claim 3 wherein said copper chelating agent is penicillamine, and said amount of penicillamine yields a penicillamine concentration in neural cells of said subject of about 0.01 to about 1 :M.

8. The method of claim 1 wherein said subject is human.

9. The method of claim 1 wherein said mutant CuZnSOD protein is encoded by a mutant sod1 gene selected from the group consisting of A4V, G93A, G37R, G41D, G85R, I112T, I113T, D90A, E100, L106, V148, H43, H46R, L38V, and L144.

10. The method of claim 9 wherein said mutant sod1 gene is A4V.

11. A method of modulating radical formation in cells previously determined to have a mutant CuZnSOD protein, said method comprising administering to said cells a copper chelating agent in an amount effective to modulate radical formation by said mutant CuZnSOD protein.

12. The method of claim 11 wherein said copper chelating agent is selected from the group consisting of diethyldithiocarbamate, penicillamine, catechol, diethylenetriaminepentaacetic acid, diisopropylsalicylate, dithizone, ethylenediaminetetraacetic acid, tetraethylenepentamine, triethylenetetramine, and tetrakis-2-(pyridylmethyl) ethylenediamine.

13. The method of claim 11 wherein said copper chelating agent is selected from the group consisting of diethyldithiocarbamate and penicillamine.

14. The method of claim 13 wherein said copper chelating agent is DDC, and said amount is about 0.001 to about 1 g of DDC per kg of said cells.

15. The method of claim 13 wherein said copper chelating agent is DDC, and said amount of DDC yields a DDC concentration in said cells of about 0.01 to about 1 :M.

16. The method of claim 13 wherein said copper chelating agent is penicillamine, and said amount is about 0.001 to about 1 g of penicillamine per kg of said cells.

17. The method of claim 13 wherein said copper chelating agent is penicillamine, and said amount of penicillamine yields a penicillamine concentration in said cells of about 0.01 to about 1 :M.

18. The method of claim 11 wherein said cells are human cells.

19. The method of claim 11 wherein said mutant sod1 gene is selected from the group consisting of A4V, G93A, G37R, G41D, G85R, I112T, I113T, D90A, E100, L106, V148, H43, H46R, L38V, and L144.

20. The method of claim 11 wherein said mutant sod1 gene is A4V.

* * * * *

UNITED STATES PATENT AND TRADEMARK OFFICE
CERTIFICATE OF CORRECTION

PATENT NO. : 5,834,457
DATED : November 10, 1998
INVENTOR(S) : Bredesen et al.

It is certified that error appears in the above-indentified patent and that said Letters Patent is hereby corrected as shown below:

Column 1, line 5, insert the following:

This invention was made with Government support under Grant Nos. AG12282, DK46828, and GM28222 awarded by the National Institutes of Health. The Government has certain rights in this invention.

Signed and Sealed this

Seventh Day of September, 1999

Attest:

Q. TODD DICKINSON

*Attesting Officer*  *Acting Commissioner of Patents and Trademarks*